United States Patent [19]

Torii et al.

[11] Patent Number: 5,656,754

[45] Date of Patent: Aug. 12, 1997

[54] PROCESS FOR PREPARING CEPHEM COMPOUNDS

[75] Inventors: Shigeru Torii, Okayama-ken; Hideo Tanaka, Oakayama; Michio Sasaoka, Tokushima; Takashi Shiroi, Tokushima; Yutaka Kameyama, Tokushima, all of Japan

[73] Assignee: Otsuka Kagaku Kabushiki Kaisha, Osaka, Japan

[21] Appl. No.: 211,119

[22] PCT Filed: Jul. 26, 1993

[86] PCT No.: PCT/JP93/01041

§ 371 Date: Mar. 22, 1994

§ 102(e) Date: Mar. 22, 1994

[87] PCT Pub. No.: WO94/02490

PCT Pub. Date: Feb. 3, 1994

[30] Foreign Application Priority Data

Jul. 27, 1992 [JP] Japan ..................... 4-220621

[51] Int. Cl.$^6$ ..................... C07D 501/16
[52] U.S. Cl. ............. 540/215; 540/222; 540/225
[58] Field of Search .................. 540/215, 222, 540/225

[56] References Cited

U.S. PATENT DOCUMENTS

| | | | |
|---|---|---|---|
| 4,870,168 | 9/1989 | Baker | 540/222 |
| 5,132,419 | 7/1992 | Lanz | 540/215 |
| 5,266,691 | 11/1993 | Farino et al. | 540/215 |
| 5,420,269 | 5/1995 | Baker | 540/205 |

FOREIGN PATENT DOCUMENTS

| | | |
|---|---|---|
| 63-307885 | 12/1988 | Japan . |
| 1-313483 | 12/1989 | Japan . |
| 3-120288 | 5/1991 | Japan . |
| 3-220195 | 9/1991 | Japan . |

OTHER PUBLICATIONS

Hideo Tanaka, Yutaka Kameyama et al., Synlett (12), 1991, pp. 888–890.
Joydeep Kant & Vittorio Farina, Tetrahedron Letters, vol. 33, No. 25, pp. 3563–3566, 1992.

Primary Examiner—Mukund J. Shah
Assistant Examiner—Deepak R. Rao
Attorney, Agent, or Firm—Kubovcik & Kubovcik

[57] ABSTRACT

The present invention provides a process for preparing a cephem compound represented by the general formula (3) characterized in that an allenyl-β-lactam compound represented by the general formula (1) is reacted with an organotin compound represented by the general formula (2) in the presence of a monovalent copper salt

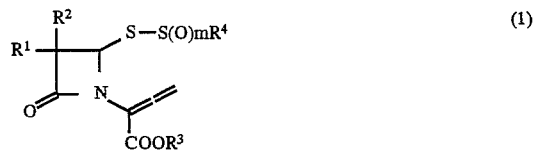

wherein $R^1$ is a hydrogen atom, halogen atom, amino or protected amino, $R^2$ is a hydrogen atom, halogen atom, lower alkoxyl, lower acyl, lower alkyl, lower alkyl having hydroxyl or protected hydroxyl as a substituent, hydroxyl or protected hydroxyl, or $R^1$ and $R^2$ form=0 when taken together, $R^3$ is a hydrogen atom or carboxylic acid protecting group, $R^4$ is aryl, aryl having a substituent, nitrogen-containing aromatic heterocyclic group or nitrogen-containing aromatic heterocyclic group having a substituent, and m is 0 or 2,

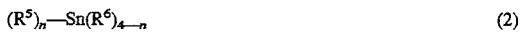

wherein $R^5$ is alkenyl, alkenyl having a substituent, aryl, aryl having a substituent, nitrogen-containing aromatic heterocyclic group or nitrogen-containing aromatic heterocyclic group having a substituent, $R^6$ is lower alkyl, and n is 1 or 2,

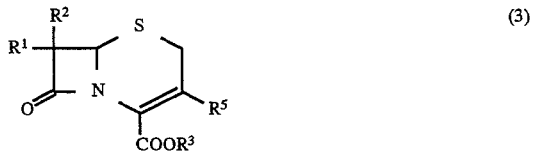

wherein $R^1$, $R^2$, $R^3$ and $R^5$ are the same as defined above.

6 Claims, No Drawings

PROCESS FOR PREPARING CEPHEM COMPOUNDS

This is a national phase application filed under 37 C.F.R. 371 of PCT/JP93/01041 filed Jul. 26, 1993.

TECHNICAL FIELD

The present invention relates to a process for preparing cephem compounds having a broad antibacterial spectrum.

BACKGROUND ART

The Witting reaction is already known as a process for preparing 3-alkenyl cephem compounds (e.g., JP-A-120288/1991, JP-A-307885/1988, etc.).

Also known as a process for preparing 3-alkenyl, 3-aryl and 3-heterocyclic cephem compounds is the process wherein a cephem compound having an elimination group L (such as fluorosulfonyloxy group or trifluoromethylsulfonyloxy group) at the C(3)- position is reacted with an organotin compound in the presence of a palladium catalyst (JP-A-220195/1991 and JP-A-313483/1989).

These processes each use a compound having a cephem skeleton as the starting material and have problems, for example, in respect of the economy of the material or the number of steps involved in preparing the material.

Further a report was recently made on a process for preparing 3-alkenyl or 3-aryl cephem compounds, i.e., a process wherein an allenyl-β-lactam compound found by us (Torii et al., Synlett, 1991, 888), represented by the general formula (1) and serving as the starting material is reacted with an organocopper reagent prepared in advance from an organotin compound and dimethyl cuprate, or an organolithium compound and cuprous iodide, or a Grignard reagent and cuprous iodide [Kant et al., Tetrahedron Letters, 33 (25), 3563 (1992)]. This process affords the desired cephem compound from an inexpensive penicillin compound by a short reaction step. With this process, however, the reaction must be conducted at an extremely low temperature (−100° to −78° C.) which is industrially infeasible, further produces an undesirable 2-cephem compound as a by-product and encounters difficulty in purifying the desired product.

An object of the present invention is to provide a novel process for preparing various cephem compounds having a broad antibacterial spectrum from an allenyl-β-lactam compound easily by a simplified reaction procedure under reaction conditions which can be industrially realized with ease, the lactam compound being readily available from an inexpensive penicillin compound by a short reaction step.

The present invention provides a process for preparing a cephem compound represented by the general formula (3) characterized in that an allenyl-β-lactam compound represented by the general formula (1) is reacted with an organotin compound represented by the general formula (2) in the presence of a monovalent copper salt

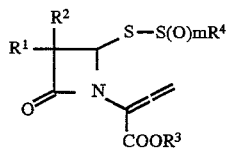

wherein $R^1$ is a hydrogen atom, halogen atom, amino or protected amino, $R^2$ is a hydrogen atom, halogen atom, lower alkoxyl, lower acyl, lower alkyl, lower alkyl having hydroxyl or protected hydroxyl as a substituent, hydroxyl or protected hydroxyl, or $R^1$ and $R^2$ form=O when taken together, $R^3$ is a hydrogen atom or carboxylic acid protecting group, $R^4$ is aryl, aryl having a substituent, nitrogen-containing aromatic heterocyclic group or nitrogen-containing aromatic heterocyclic group having a substituent, and m is 0 or 2, $$(R^5)_n—Sn(R^6)_{4-n} \quad (2)$$

wherein $R^5$ is alkenyl, alkenyl having a substituent, aryl, aryl having a substituent, nitrogen-containing aromatic heterocyclic group or nitrogen-containing aromatic heterocyclic group having a substituent, $R^6$ is lower alkyl, and n is 1 or 2, $$\begin{array}{c} R^2 \quad S \\ R^1 \underset{O}{\overset{}{\diagup}} \underset{N}{\diagdown} \underset{COOR^3}{\diagdown} R^5 \end{array} \quad (3)$$

wherein $R^1$, $R^2$, $R^3$ and $R^5$ are the same as defined above.

Examples of groups mentioned herein are as follows. The term "halogen atom" as used hereinafter means, for example, fluorine, chlorine, bromine or iodine atom unless otherwise specified. The term "lower alkyl" means a straight-chain or branched $C_{1-4}$ alkyl group such as methyl, ethyl, n-propyl, isopropyl, n-butyl, isobutyl, sec-butyl or tert-butyl. The term "aryl" means, for example, phenyl, naphthyl or the like.

Exemplary of the protected amino represented by $R^1$ are phenoxyacetamido, p-methylphenoxyacetamido, p-methoxyphenoxyacetamido, p-chlorophenoxyacetamido, p-bromophenoxyacetamido, phenylacetamido, p-methylphenylacetamido, p-methoxyphenylacetamido, p-chlorophenylacetamido, p-bromophenylacetamido, phenylmonochloroacetamido, phenyldichloroacetamido, phenylhydroxyacetamido, phenylacetoxyacetamido, α-oxophenylacetamido, thienylacetamido, benzamido, p-methylbenzamido, p-tert-butylbenzamido, p-methoxybenzamido, p-chlorobenzamido and p-bromobenzamido groups, the groups disclosed in Theodora W. Greene, "Protective Groups in Organic Synthesis" (hereinafter referred to merely as the "literature"), Chap. 7 (pp. 218~287), phenylglycylamido group, phenylglycylamido groups having protected amino, p-hydroxyphenylglycylamido group, and p-hydroxyphenylglycylamido groups having protected amino and/or protected hydroxyl. Examples of protective groups for amino are those disclosed in the literature, Chap. 7 (pp. 218~287). Examples of protective groups for the hydroxyl of p-hydroxyphenylglycylamido group are those disclosed in the literature, Chap.2 (pp. 10~72).

Exemplary of the lower alkoxyl represented by $R^2$ are straight-chain or branched $C_{1-4}$ alkoxyl groups such as methoxy, ethoxy, n-propoxy, isopropoxy, n-butoxy, isobutoxy, sec-butoxy and tert-butoxy groups.

Exemplary of the lower acyl represented by $R^2$ are straight-chain or branched $C_{1-4}$ acyl groups such as formyl, acetyl, propionyl, butyryl and isobutyryl.

Examples of protective groups for the protected hydroxyl in the lower alkyl represented by $R^2$ and substituted with hydroxyl or protected hydroxyl, and for the protected hydroxyl represented by $R^2$ are those disclosed in the literature, Chap. 2 (pp. 10~72). The substituted lower alkyl represented by $R^2$ may have as its substituent(s) one or at least two same or different groups selected from among hydroxyl and the protected hydroxyl groups. Such substituent(s) may be positioned on at least one carbon atom of the alkyl.

Exemplary of the carboxylic acid protecting group represented by $R^3$ are benzyl, p-methoxybenzyl, p-nitrobenzyl, diphenylmethyl, trichloroethyl, tert-butyl, and those disclosed in the literature, Chap. 5 (pp. 152–192).

While $R^4$ represents a nitrogen-containing aromatic heterocyclic group which may have a substituent or substituents, exemplary of the nitrogen-containing aromatic hetrocyclic group are thiazol-2-yl, thiadiazol-2-yl, benzothiazol-2-yl, oxazol-2-yl, benzoxazol-2-yl, imidazol-2-yl, benzoimidazol-2-yl, pyrimidinyl, pyridyl and the like.

Exemplary of the substituent which may be substituted in the aryl or nitrogen-containing aromatic heterocyclic group represented by $R^4$ are halogen atoms, hydroxyl, nitro, cyano, aryl, lower alkyl, amino, mono lower alkylamino, di lower alkylamino, mercapto, alkylthio or arylthio represented by the group $R^7S$— (wherein $R^7$ is lower alkyl or aryl), formyloxy, acyloxy represented by the group $R^7COO$— (wherein $R^7$ is as defined above), formyl, acyl represented by the group $R^7CO$— (wherein $R^7$ is as defined above), alkoxyl or aryloxy represented by $R^7O$— (wherein $R^7$ is as defined above), carboxyl, alkoxycarbonyl or aryloxycarbonyl represented by the group $R^7OCO$— (wherein $R^7$ is as defined above), etc. The aryl or nitrogen-containing aromatic heterocyclic group represented by $R^4$ may have one or at least two same or different groups selected from among the above substituents.

Examples of the alkenyl represented by $R^5$ are vinyl, 1-propenyl, propene-2-yl, 2-methylpropene-1-yl, (E)-1-styryl, trifluorovinyl, 1-methoxypropene-1-yl, 1-cyclohexenyl, 4-tert-butylcyclohexen-1-yl, (E)-2-tributylstannylvinyl, allenyl, 1-butene-1-yl and the like. Examples of the nitrogen-containing aromatic heterocyclic groups are pyridyl, pyrazyl, pyrimidinyl, pyridazinyl, pyrrolyl, imidazolyl, pyrazolyl, isothiazolyl, isooxazolyl, purinyl, pteridinyl and the like.

$R^5$ represents alkenyl, aryl or nitrogen-containing aromatic heterocyclic group which may have a substituent or substituents, examples of which are those mentioned for $R^4$. The alkenyl, aryl or nitrogen-containing aromatic heterocyclic group represented by $R^5$ may have one or at least two same or different groups selected from among the foregoing substituents.

The allenyl-β-lactam compound of the formula (1) for use as the starting material of the present invention is prepared, for example, by the process disclosed in literature (Torii et al., Synlett, 1991, 888) (see Reference Examples given later).

According to the invention, the allenyl-β-lactam compound represented by the formula (1) and prepared by the above process is reacted with an organotin compound represented by the formula (2) in the presence of a monovalent copper salt, whereby a cephem compound represented by the formula (3) is obtained.

More specific examples of organotin compounds represented by the formula (2) are vinyltributyltin, divinyldibutyltin, (Z)-1-propenyltributyltin, (E)-1-styryltributyltin, 1-tributylstannyl-1-methylpropene, 1-tributylstannyl-2-methylpropene, (trifluorovinyl) tributyltin, 1-methoxy-1-(tributylstannyl)ethylene, 1-tributylstannyl-cyclohexene, (4-tert-butylcyclohexen-1-yl)trimethyltin, (4-tert-butylcylcohexen-1-yl)tributyltin, (E)-1,2-bis(tributylstannyl)ethylene, allenyltributyltin, 1-tributylstannyl-1-butene, phenyltributyltin, (p-methoxyphenyl)tributyltin, [p-(trifluoromethyl)phenyl]-tributyltin, 2-tributylstannylpyridine, 2-tributylstannyl-pyrazine, 2-tributylstannylpyrimidine, 3-tributylstannyl-pyridazine, 1-methyl-2-(tributylstannyl)pyrrole, 1-methyl-2-(tributylstannyl)imidazole, 1-methyl-3-(tributylstannyl)-pyrazole, 3-tributylstannylisothiazole, 3-tributylstannyl-isooxazole, 7-methyl-8-tributylstannylpurine, 2-tributylstannylpteridine and the like. These organotin compounds represented by the formula (2) are used usually in an amount of 1 to 3 moles, preferably 1 to 2 moles, per mole of the compound of the formula (1).

Examples of monovalent copper salts are cuprous halides such as cuprous chloride, cuprous bromide and cuprous iodide, etc. These copper salts are used in an amount of 0.5 to 10 moles, preferably 1 to 3 moles, per mole of the compound of the formula (1).

Examples of solvents are dimethylacetamide, dimethylformamide, 1-methyl-2-pyrrolidinone, hexamethyl phosphoric triamide and like amides, acetonitrile, propionitrile, butyronitrile, isobutyronitrile, valeronitrile and like nitriles, dimethyl sulfoxide, etc. These solvents may be used singly, or at least two of them may be used in admixture. Also usable are solvent mixtures consisting primarily of such a solvent and further comprising other usual solvents, which are, for example, lower alkyl esters of lower carboxylic acids such as methyl formate, ethyl formate, propyl formate, butyl formate, methyl acetate, ethyl acetate, propyl acetate, butyl acetate, methyl propionate and ethyl propionate, ethers such as diethyl ether, ethyl propyl ether, ethyl butyl ether, dipropyl ether, diisopropyl ether, dibutyl ether, methyl cellosolve and dimethoxyethane, cyclic ethers such as tetrahydrofuran and dioxane, substituted or unsubstituted aromatic hydrocarbons such as benzene, toluene, xylene, chlorobenzene and anisole, hydrocarbon halides such as dichloromethane, chloroform, dichloroethane, trichloroethane, dibromoethane, propylene dichloride, carbon tetrachloride and Freons, hydrocarbons such as pentane, hexane, heptane and octane, and cycloalkanes such as cyclopentane, cyclohexane, cycloheptane and cyclooctane. Especially preferred solvents are solvent mixtures consisting primarily of dimethylformamide, 1-methyl-2-pyrrolidinone or dimethyl sulfoxide. These solvents are used in an amount of about 0.5 to about 200 liters, preferably about 1 to about 50 liters, per kilogram of the compound of the formula (1). The reaction is conducted at $-10°$ C. to $80°$ C., preferably $0°$ C. to $50°$ C. The compound of the present invention can be obtained in the form of a substantially pure product by subjecting the resulting reaction mixture to extraction or crystallization in the usual manner, while the product can of course be purified by other method.

BEST MODE OF CARRYING OUT THE INVENTION

The present invention will be clarified in greater detail with reference to the following examples. Ph stands for phenyl.

EXAMPLE 1 p-Methoxybenzyl 7-phenylacetamido-3-vinylcephalosporanate

A 100 mg quantity of a compound of the formula (1) ($R^1$=phenylacetamido, $R^2$=H, $R^3$=p-methoxybenzyl, $R^4$=phenyl, m=2, 1a) and 20.5 mg of cuprous chloride were weighed out, to which 1 ml of 1-methyl-2-pyrrolidinone was added. With addition of 76 μl of vinyltributyltin, the mixture was stirred at room temperature for reaction. Ethyl acetate and 2% hydrochloric acid were added to the reaction mixture for extraction, and the resulting organic layer was washed with water and a common salt aqueous solution. The organic layer was dried over sodium sulfate and distilled at a reduced pressure to remove the solvent, affording crystals. When purified with a silica gel column (benzene/ethyl acetate=6/1), the crude crystals gave 72.3 mg (yield 90%) of a compound of the formula (3) ($R^1$=phenylacetamido, $R^2$=H, $R^3$=p-methoxybenzyl, $R^5$=vinyl, 3a)

EXAMPLE 2

The same reaction as in Example 1 was repeated using cuprous bromide instead of cuprous chloride, whereby the corresponding compound 3a of the formula (3) was obtained in a yield of 87%.

EXAMPLE 3

The same reaction as in Example 1 was conducted using cuprous iodide instead of cuprous chloride, whereby the corresponding compound 3a of the formula (3) was obtained in a yield of 80%.

EXAMPLE 4

The same reaction as in Example 1 was conducted using N,N-dimethylformamide instead of 1-methyl-2-pyrrolidinone, whereby the corresponding compound 3a of the formula (3) was obtained in a yield of 82%.

EXAMPLE 5

The same reaction as in Example 1 was conducted using a compound of the formula (1) ($R^1$=phenylacetamido, $R^2$=H, $R^3$=p-methoxybenzyl, $R^4$=benzothiazol-2-yl, m=0, 1b) instead of the compound of the formula (1) ($R^1$=phenylacetamido, $R^2$=H, $R^3$=p-methoxybenzyl, $R^4$=phenyl, m=2, 1a), whereby the corresponding compound 3a of the formula (3) was obtained in a yield of 82%.

EXAMPLES 6 to 11

The same reaction as in Example 1 was conducted using the compound of the formula (1) ($R^1$=phenylacetamido, $R^2$=H, $R^3$=p-methoxybenzyl, $R^4$=phenyl, m=2, 1a) and a compound represented by the formula (2) ($R^6$=butyl, n=1) and having a substituent shown in Table 1 as $R^5$, whereby the corresponding compound of the formula (3) ($R^1$=phenylacetamido, $R^2$=H, $R^3$=p-methoxybenzyl, see Table 1 for $R^5$) was obtained.

TABLE 1

| Example | $R^5$ | yield of compound (3) | |
|---|---|---|---|
| 6 | propene-2-yl | 91% | 3b |
| 7 | (Z)-1-propenyl | 89% | 3c |
| 8 | 2-methylpropene-1-yl | 89% | 3d |
| 9 | allenyl | 80% | 3e |
| 10 | phenyl | 85% | 3f |
| 11 | (E)-1-styryl | 73% | 3g |

EXAMPLES 12 to 26

The same reaction as in Example 1 was conducted using a compound of the formula (1) (see Table 2 for $R^1$ and $R^3$, $R^2$=H, $R^4$=phenyl, m=2) and a compound represented by the formula (2) ($R^6$=butyl, n=1) and having a substituent shown in Table 2 as $R^5$, whereby the corresponding compound of the formula (3) (see Table 2 for $R^1$, $R^3$ and $R^5$, $R^2$=H) was obtained.

TABLE 2

| Ex. | $R^1$ | $R^3$ | $R^5$ | yield (%) |
|---|---|---|---|---|
| 12 | phenylacetamido | diphenylmethyl | (Z)-1-propenyl | 88 |
| 13 | phenylacetamido | diphenylmethyl | allenyl | 81 |
| 14 | phenylacetamido | diphenylmethyl | phenyl | 83 |
| 15 | phenylacetamido | p-nitrobenzyl | (Z)-1-propenyl | 89 |
| 16 | phenylacetamido | p-nitrobenzyl | allenyl | 78 |
| 17 | phenylacetamido | p-methoxybenzyl | (Z)-1-propenyl | 90 |
| 18 | phenylacetamido | p-methoxybenzyl | allenyl | 82 |
| 19 | phenylacetamido | p-methoxybenzyl | phenyl | 85 |
| 20 | phenylacetamido | diphenylmethyl | (Z)-1-propenyl | 89 |
| 21 | phenylacetamido | p-nitrobenzyl | (Z)-1-propenyl | 90 |
| 22 | phenylacetamido | p-nitrobenzyl | allenyl | 80 |
| 23 | H | p-methoxybenzyl | (Z)-1-propenyl | 92 |
| 24 | H | p-methoxybenzyl | allenyl | 83 |
| 25 | H | diphenylmethyl | (Z)-1-propenyl | 90 |
| 26 | H | diphenylmethyl | allenyl | 81 |

REFERENCE EXAMPLE 1

Preparation of allenyl-βlactam of formula (1)

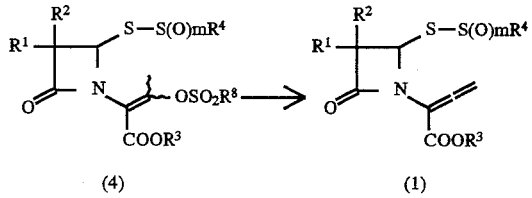

One gram of a compound of the formula (4) ($R^1$=phenylacetamido, $R^2$=H, $R^3$=p-methoxybenzyl, $R^4$=phenyl, $R^8$=trifluoromethyl, m=2) was dissolved in 10 ml of N,N-dimethylformamide. The solution was cooled to −30° C., and 0.43 ml of triethylamine was thereafter added to the solution, followed by stirring at the same temperature for 1 hour. The reaction mixture was subjected to extraction with ethyl acetate, and the extract was washed with water and thereafter dried over anhydrous sodium sulfate. When concentrated at a reduced pressure, the extract gave the corresponding compound of the formula (1) ($R^1$, $R^2$, $R^3$, $R^4$ and m are as defined above, 1a) in a yield of 99%.

REFERENCE EXAMPLE 2

The same reaction as in Reference Example 1 was conducted using another compound of the formula (4) ($R^1$=phenylacetamido, $R^2$=H, $R^3$=diphenylmethyl, $R^4$=benzothiazol-2-yl, $R^8$=trifluoromethyl, m=0) instead of the compound of the formula (4) ($R^1$=phenylacetamido, $R^2$=H, $R^3$=p-methoxybenzyl, $R^4$=phenyl, $R^8$=trifluoromethyl, m=2), whereby the corresponding compound of the formula (1) ($R^1$, $R^2$ $R^3$, $R^4$ and m are as defined above, 1c) was obtained in a yield of 99%.

INDUSTRIAL APPLICABILITY

The desired useful cephem compound represented by the general formula (3) and having a broad antibacterial spectrum can be prepared by the invention at ambient temerature (room temperature) in a high yield without the necessity of preparing an organocopper reagent or the like. The invention advantageously affords the desired product without necessitating special purification since the process does not involve formation of undesirable 2-cephem compounds as by-products.

We claim:

1. A process for preparing a cephem compound represented by the formula (3) characterized in that an allenyl-β-lactam compound represented by the formula (1) is reacted at a temperature of from −10° to 80° C. with an organotin compound represented by the formula (2) in the presence of a monovalent copper salt

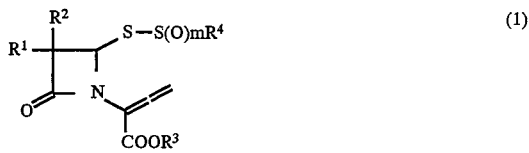

wherein $R^1$ is a hydrogen atom, halogen atom, amino or protected amino, $R^2$ is a hydrogen atom, halogen atom, lower alkoxyl, lower acyl, lower alkyl, lower alkyl having hydroxyl or protected hydroxyl as a substituent, hydroxyl or protected hydroxyl, or $R^1$ and $R^2$ form=O when taken together, $R^3$ is a hydrogen atom or carboxylic acid protecting group, $R^4$ is phenyl, naphthyl, a nitrogen-containing aromatic heterocyclic group selected from the group consisting of thiazol-2-yl, thiadiazol-2-yl, benzothiazol-2-yl, oxazol-2-yl, benzoxazol-2-yl, imidazol-2-yl, benzoimidazol-2-yl, pyrimidinyl, and pyridyl, wherein said phenyl naphthyl or nitrogen-containing aromatic heterocyclic group may have at least one substituent selected from the group consisting of halogen, hydroxyl, nitro, cyano, phenyl, naphthyl, lower alkyl, amino, mono lower alkylamino, di lower alkylamino, mercapto, $R^7S—$, formyl, formyloxy, $R^7COO—$, $R^7CO—$, $R^7O—$, $R^7OCO—$, and carboxyl, and m is 0 or 2,

wherein $R^5$ is alkenyl, phenyl, naphthyl, a nitrogen-containing aromatic heterocyclic group selected from the group consisting of thiazol-2-yl, thiadiazol-2-yl, benzothiazol-2-yl, oxazol-2-yl, benzoxazol-2-yl, imidazol-2-yl, benzoimidazol-2-yl, pyrimidinyl, and pyridyl, wherein said alkenyl, phenyl, naphthyl or nitrogen-containing aromatic heterocyclic group may have at least one substituent selected from the group consisting of halogen, hydroxyl, nitro, cyano, phenyl, naphthyl, lower alkyl, amino, mono lower alkylamino, di lower alkylamino, mercapto, $R^7S—$, formyl, formyloxy, $R^7COO—$, $R^7CO—$, $R^7O—$, $R^7OCO—$, and carboxyl, $R^6$ is lower alkyl, $R^7$ is $C_{1-4}$ alkyl, phenyl or naphthyl, and n is 1 or 2,

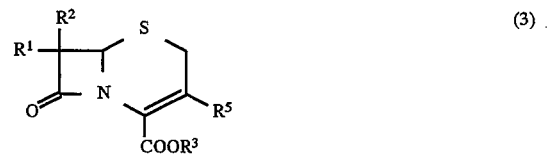

wherein $R^1$, $R^2$, $R^3$ and $R^5$ are the same as defined above.

2. A process as defined in claim 1 wherein the monovalent copper salt is cuprous chloride, cuprous bromide or cuprous iodide.

3. A process as defined in claim 1, wherein from 1 to 3 moles of the organotin compound is reacted per mole of the allenyl-β-lactam compound.

4. A process as defined in claim 1, wherein from 0.5 to 10 moles of the monovalent copper salt is present per mole of the allenyl-β-lactam compound.

5. A process as defined in claim 4, wherein from 1 to 3 moles of the monovalent copper salt is present per mole of the allenyl-β-lactam compound.

6. A process as defined in claim 1, wherein the allenyl-β-lactam is reacted with the organotin compound at a temperature of from 0° to 50° C.

* * * * *